US011319366B2

(12) United States Patent
Jiang et al.

(10) Patent No.: US 11,319,366 B2
(45) Date of Patent: May 3, 2022

(54) ANTIBODY FACILITATING PROGRAMMED NECROSIS OF CELLS AND APPLICATION THEREOF

(71) Applicant: SHANGHAI JW INFLINHIX CO., LTD., Shanghai (CN)

(72) Inventors: Shisong Jiang, Beijing (CN); Wenshu Lu, Shanghai (CN)

(73) Assignee: SHANGHAI JW INFLINHIX CO., LTD., Shanghai (CN)

( * ) Notice: Subject to any disclaimer, the term of this patent is extended or adjusted under 35 U.S.C. 154(b) by 446 days.

(21) Appl. No.: 15/745,624

(22) PCT Filed: Jul. 18, 2016

(86) PCT No.: PCT/CN2016/090322
§ 371 (c)(1),
(2) Date: Jan. 17, 2018

(87) PCT Pub. No.: WO2017/012525
PCT Pub. Date: Jan. 26, 2017

(65) Prior Publication Data
US 2019/0062417 A1  Feb. 28, 2019

(30) Foreign Application Priority Data
Jul. 17, 2015 (CN) .......................... 201510424724.3

(51) Int. Cl.
| C07K 16/24 | (2006.01) |
| C12N 15/63 | (2006.01) |
| C12N 5/10 | (2006.01) |
| A61K 39/395 | (2006.01) |
| G01N 33/577 | (2006.01) |
| G01N 33/564 | (2006.01) |
| G01N 33/68 | (2006.01) |

(52) U.S. Cl.
CPC .......... *C07K 16/241* (2013.01); *A61K 39/395* (2013.01); *C07K 16/24* (2013.01); *C12N 5/10* (2013.01); *C12N 15/63* (2013.01); *G01N 33/564* (2013.01); *G01N 33/577* (2013.01); *G01N 33/6863* (2013.01); *C07K 2317/34* (2013.01); *C07K 2317/565* (2013.01); *C07K 2317/73* (2013.01); *G01N 2800/102* (2013.01)

(58) Field of Classification Search
None
See application file for complete search history.

(56) References Cited

U.S. PATENT DOCUMENTS

| 5,876,691 A * | 3/1999 | Chester ................ C07K 16/065 424/1.49 |
| 7,528,237 B2 | 5/2009 | Rathjen et al. | |
| 2006/0228358 A1* | 10/2006 | Lawson ................... A61P 37/06 424/145.1 |
| 2009/0136516 A1* | 5/2009 | Tedder .................... A61P 21/04 424/153.1 |

FOREIGN PATENT DOCUMENTS

CN    103096927    5/2013

OTHER PUBLICATIONS

Nishioka, Y., et al. Organization and complete sequence of the identical embryonic and plasmacytoma kappa V-region genes. J. Biol. Chem., 1980, 255(8):3691-3694.*
NCBI protein BLAST search results for QLVVPSE, Aug. 30, 2019.*
Cappellano, G., et al. Anti-cytokine autoantibodies in autoimmune diseases. Am. J. Clin. Exp. Immunol., 2012, 1(2):136-146.*
Chan et al., "Signaling by the TNF receptor superfamily and T cell homeostasis", Immunity, vol. 13, 419-422, Oct. 2000, by Cell Press, 4 pages.
Thoma et al., "Identification of a 60-kD tumor necrosis factor (TNF) receptor as the major signal transducing component in TNF responses", J Exp. Med, The Rockefeller University Press, vol. 172, Oct. 1990, pp. 1019-1023.
Idriss et al., "TNFα and the TNF receptor superfamily: Structure-function relationship(s)", Microscopy Research and Technique, first published Jul. 6, 2000, 12 pages.
Herreweghe et al., "Tumor necrosis factor-mediated cell death: to break or to burst, that's the question", Cellular and Molecular Life Sciences, published online Mar. 4, 2010, pp. 1567-1579.
Kono et al., "How dying cells alert the immune system to danger", Nature Reviews, vol. 8, Apr. 2008, pp. 279-289.
Declercq et al., "RIP kinases at the crossroads of cell death and survival", Leading Edge Minireview, Cell 138 Jul. 24, 2009, pp. 229-232.
Hitomi et al., "Identification of a molecular signaling network that regulates a cellular necrotic cell death pathway", Cell 135, Dec. 26, 2008, pp. 1311-1323.
Galluzzi et al., "Necroptosis: a specialized pathway of programmed necrosis", Cell 135, Dec. 26, 2008, pp. 1161-1163.
Vandenabeele et al., "Molecular mechanisms of necroptosis: an ordered cellular explosion", Nature Reviews Molecular Cell Biology vol. 11, Oct. 2010, pp. 700-714.
Berghe et al., "Necroptosis, necrosis and secondary necrosis converge on similar cellular disintegration features", Cell Death and Differentiation (2010), pp. 922-930.
Chan et al., "A role for tumor necrosis factor receptor-2 and receptor-interacting protein in programmed necrosis and antiviral responses", The journal of Biological Chemistry, vol. 278, No. 51, Issue of Dec. 19, 2003, 12 pages.

(Continued)

*Primary Examiner* — Elizabeth C. Kemmerer
(74) *Attorney, Agent, or Firm* — Hamre, Schumann, Mueller & Larson, P.C.

(57) ABSTRACT

The present invention provides an antibody facilitating programmed necrosis of cells. The antibody can cause programmed necrosis of cells in the presence of tumor necrosis factor (TNF). Therefore, an inhibitor for the antibody can be used in the treatment of inflammatory diseases. Further, the present invention provides the application of the antibody facilitating programmed necrosis of cells in the inflammatory disease prognosis.

18 Claims, 7 Drawing Sheets
(1 of 7 Drawing Sheet(s) Filed in Color)
Specification includes a Sequence Listing.

(56) References Cited

OTHER PUBLICATIONS

Marc Feldmann, "Translating molecular insights in autoimmunity into effective therapy", first published online as a Review in Advance on Nov. 13, 2008, 30 pages.
N Scheinfeld, "A comprehensive review and evaluation of the side effects of the tumor necrosis factor alpha blockers etanercept, infliximab and adalimumab", Journal of Dermatological Treatment, 2004, pp. 280-294.
Gunther et al., "Apoptosis, necrosis and necroptosis: cell death regulation in the intestinal epithelium", Recent advances in basic science, 2011, pp. 1062-1071.
Rock et al., "The inflammatory response to cell death", www.annualreviews.org, vol. 3, 2008, 30 pages.
Linkermann et al., "Necroptosis", The New England Journal of Medicine, Jan. 30, 2014, 11 pages.
International Search Report for international appl. No. PCT/CN2016/090322, dated Oct. 25, 2016 (5 pages, including English translation).

* cited by examiner

SEQUENCE LISTING

```
<160> NUMBER OF SEQ ID NOS: 27

<210> SEQ ID NO 1
<211> LENGTH: 11
<212> TYPE: PRT
<213> ORGANISM: Homo sapiens

<400> SEQUENCE: 1

Arg Ala Ser Gly Asn Ile His Ile Tyr Leu Ala
1               5                   10

<210> SEQ ID NO 2
<211> LENGTH: 33
<212> TYPE: DNA
<213> ORGANISM: Homo sapiens

<400> SEQUENCE: 2
cgagcaagtg ggaatattca catttattta gca                                    33
```

<210> SEQ ID NO 3
<211> LENGTH: 7
<212> TYPE: PRT
<213> ORGANISM: Homo sapiens

<400> SEQUENCE: 3

Asn Ala Lys Thr Leu Ala Asp
1               5

<210> SEQ ID NO 4
<211> LENGTH: 21
<212> TYPE: DNA
<213> ORGANISM: Homo sapiens

<400> SEQUENCE: 4
aatgcaaaaa ccttagcaga t                                              21

<210> SEQ ID NO 5
<211> LENGTH: 9
<212> TYPE: PRT
<213> ORGANISM: Homo sapiens

<400> SEQUENCE: 5

Gln His Phe Trp Ser Ile Pro Trp Thr
1               5

<210> SEQ ID NO 6
<211> LENGTH: 27
<212> TYPE: DNA
<213> ORGANISM: Homo sapiens

<400> SEQUENCE: 6
caacattttt ggagtattcc gtggacg                                        27

<210> SEQ ID NO 7
<211> LENGTH: 107
<212> TYPE: PRT
<213> ORGANISM: Homo sapiens

<400> SEQUENCE: 7

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Ile Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ile Pro Trp
                85                  90                  95

Thr Phe Gly Gly Gly Thr Lys Leu Glu Ile Lys
            100                 105

<210> SEQ ID NO 8
<211> LENGTH: 321
<212> TYPE: DNA
<213> ORGANISM: Homo sapiens

<400> SEQUENCE: 8

```
gacatccaga tgactcagtc tccagcctcc ctatctgctt ctgtgggaga aactgtcacc      60
atcacatgtc gagcaagtgg gaatattcac atttatttag catggtatca gcagaaacag    120
ggaaaatctc ctcagctcct ggtctataat gcaaaaacct agcagatgg tgtgccatca    180 aggttcagtg gcagtggatc aggaacacaa tattctctca agatcaacag cctgcagcct    240
gaagattttg ggagttatta ctgtcaacat ttttggagta ttccgtggac gttcggtgga    300
ggcaccaagc tggaaatcaa a                                              321
```

```
<210> SEQ ID NO 9
<211> LENGTH: 107
<212> TYPE: PRT
<213> ORGANISM: Homo sapiens

<400> SEQUENCE: 9
```

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
                100                 105

```
<210> SEQ ID NO 10
<211> LENGTH: 214
<212> TYPE: PRT
<213> ORGANISM: Homo sapiens

<400> SEQUENCE: 10
```

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Ile Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ile Pro Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
        180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 11
<211> LENGTH: 642
<212> TYPE: DNA
<213> ORGANISM: Homo sapiens

<400> SEQUENCE: 11
gacatccaga tgactcagtc tccagcctcc ctatctgctt ctgtgggaga aactgtcacc      60
atcacatgtc gagcaagtgg gaatattcac atttatttag catggtatca gcagaaacag    120
ggaaaatctc ctcagctcct ggtctataat gcaaaaacct tagcagatgg tgtgccatca    180
aggttcagtg gcagtggatc aggaacacaa tattctctca agatcaacag cctgcagcct    240
gaagattttg ggagttatta ctgtcaacat ttttggagta ttccgtggac gttcggtgga    300
ggcaccaagc tggaaatcaa acgggctgat gctgcaccaa ctgtatccat cttcccacca    360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag cacccctcacg   540 ttgaccaagg acgagtatga acgacataac agctatacct gtgaggccac tcacaagaca    600
tcaacttcac ccattgtcaa gagcttcaac aggaatgagt gt                       642

<210> SEQ ID NO 12
<211> LENGTH: 5
<212> TYPE: PRT
<213> ORGANISM: Homo sapiens

<400> SEQUENCE: 12

Asn Tyr Gly Met Asn
1               5

<210> SEQ ID NO 13
<211> LENGTH: 15
<212> TYPE: DNA
<213> ORGANISM: Homo sapiens

<400> SEQUENCE: 13
aactatggaa tgaac                                                      15

<210> SEQ ID NO 14
<211> LENGTH: 20
<212> TYPE: PRT
<213> ORGANISM: Homo sapiens

<400> SEQUENCE: 14

Trp Ile Asn Thr Tyr Thr Gly Glu Pro Thr Tyr Ala Asp Asp Phe Lys
1               5                   10                  15

Gly Arg Phe Ala
            20

<210> SEQ ID NO 15

<211> LENGTH: 60
<212> TYPE: DNA
<213> ORGANISM: Homo sapiens

<400> SEQUENCE: 15
tggataaaca cctacactgg agagccaaca tatgctgatg acttcaaggg acggtttgcc    60

<210> SEQ ID NO 16
<211> LENGTH: 9
<212> TYPE: PRT
<213> ORGANISM: Homo sapiens

<400> SEQUENCE: 16

His Tyr Arg Tyr Ala Trp Phe Pro Tyr
1               5

<210> SEQ ID NO 17
<211> LENGTH: 27
<212> TYPE: DNA
<213> ORGANISM: Homo sapiens

<400> SEQUENCE: 17
cactataggt acgcctggtt tccttac    27

<210> SEQ ID NO 18
<211> LENGTH: 118
<212> TYPE: PRT
<213> ORGANISM: Homo sapiens

<400> SEQUENCE: 18

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Asn Thr Ala Tyr
65                  70                  75                  80

Leu Gln Ile Asn Asn Leu Arg Asn Glu Gly Met Ala Thr Tyr Phe Cys
                85                  90                  95

Ala Arg His Tyr Arg Tyr Ala Trp Phe Pro Tyr Trp Gly Gln Gly Thr
            100                 105                 110

Leu Val Thr Val Ser Ala
        115

<210> SEQ ID NO 19
<211> LENGTH: 354
<212> TYPE: DNA
<213> ORGANISM: Homo sapiens

<400> SEQUENCE: 19
cagatccagt tggtgcagtc tggacctgag ctgaagaagc ctggagagac agtcaagatc    60
tcctgcaagg cttctggata taccttcaca aactatggaa tgaactgggt gaagcaggct   120
ccaggaaagg gtttaaagtg gatgggctgg ataaacacct acactggaga gccaacatat   180
gctgatgact tcaagggacg gtttgccttc tctttggaaa cctctgccaa cactgcctat   240
ttgcagatca acaacctcag aaatgagggc atggctacat atttctgtgc aagacactat   300

```
aggtacgcct ggtttcctta ctggggccaa gggactctgg tcactgtctc tgca         354
```

<210> SEQ ID NO 20
<211> LENGTH: 336
<212> TYPE: PRT
<213> ORGANISM: Homo sapiens

<400> SEQUENCE: 20

Ala Lys Thr Thr Pro Pro Ser Val Tyr Pro Leu Ala Pro Gly Cys Gly
1               5                   10                  15

Asp Thr Thr Gly Ser Ser Val Thr Leu Gly Cys Leu Val Lys Gly Tyr
            20                  25                  30

Phe Pro Glu Ser Val Thr Val Thr Trp Asn Ser Gly Ser Leu Ser Ser
        35                  40                  45

Ser Val His Thr Phe Pro Ala Leu Leu Gln Ser Gly Leu Tyr Thr Met
    50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                85                  90                  95

Leu Glu Pro Ser Gly Pro Ile Ser Thr Ile Asn Pro Cys Pro Pro Cys
            100                 105                 110

Lys Glu Cys His Lys Cys Pro Ala Pro Asn Leu Glu Gly Gly Pro Ser
        115                 120                 125

Val Phe Ile Phe Pro Pro Asn Ile Lys Asp Val Leu Met Ile Ser Leu
    130                 135                 140

Thr Pro Lys Val Thr Cys Val Val Val Asp Val Ser Glu Asp Asp Pro
145                 150                 155                 160

Asp Val Gln Ile Ser Trp Phe Val Asn Asn Val Glu Val His Thr Ala
                165                 170                 175

Gln Thr Gln Thr His Arg Glu Asp Tyr Asn Ser Thr Ile Arg Val Val
            180                 185                 190

Ser Thr Leu Pro Ile Gln His Gln Asp Trp Met Ser Gly Lys Glu Phe
        195                 200                 205

Lys Cys Lys Val Asn Asn Lys Asp Leu Pro Ser Pro Ile Glu Arg Thr
    210                 215                 220

Ile Ser Lys Ile Lys Gly Leu Val Arg Ala Pro Gln Val Tyr Ile Leu
225                 230                 235                 240

Pro Pro Pro Ala Glu Gln Leu Ser Arg Lys Asp Val Ser Leu Thr Cys
                245                 250                 255

Leu Val Val Gly Phe Asn Pro Gly Asp Ile Ser Val Glu Trp Ala Ser
            260                 265                 270

Asn Gly His Thr Glu Glu Asn Tyr Lys Asp Thr Ala Pro Val Leu Asp
        275                 280                 285

Ser Asp Gly Ser Tyr Phe Ile Tyr Ser Lys Leu Asn Met Lys Thr Ser
    290                 295                 300

Lys Trp Glu Lys Thr Asp Ser Phe Ser Cys Asn Val Arg His Glu Gly
305                 310                 315                 320

Leu Lys Asn Tyr Tyr Leu Lys Lys Thr Ile Ser Arg Ser Pro Gly Lys
                325                 330                 335

<210> SEQ ID NO 21
<211> LENGTH: 454
<212> TYPE: PRT
<213> ORGANISM: Homo sapiens

<400> SEQUENCE: 21

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Asn Thr Ala Tyr
65                  70                  75                  80

Leu Gln Ile Asn Asn Leu Arg Asn Glu Gly Met Ala Thr Tyr Phe Cys
                85                  90                  95

Ala Arg His Tyr Arg Tyr Ala Trp Phe Pro Tyr Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Cys Gly Asp Thr Thr Gly Ser Ser Val Thr Leu Gly
    130                 135                 140

Cys Leu Val Lys Gly Tyr Phe Pro Glu Ser Val Thr Val Thr Trp Asn
145                 150                 155                 160

Ser Gly Ser Leu Ser Ser Val His Thr Phe Pro Ala Leu Leu Gln
                165                 170                 175

Ser Gly Leu Tyr Thr Met Ser Ser Ser Val Thr Val Pro Ser Ser Thr
            180                 185                 190

Trp Pro Ser Gln Thr Val Thr Cys Ser Val Ala His Pro Ala Ser Ser
        195                 200                 205

Thr Thr Val Asp Lys Lys Leu Glu Pro Ser Gly Pro Ile Ser Thr Ile
    210                 215                 220

Asn Pro Cys Pro Pro Cys Lys Glu Cys His Lys Cys Pro Ala Pro Asn
225                 230                 235                 240

Leu Glu Gly Gly Pro Ser Val Phe Ile Phe Pro Pro Asn Ile Lys Asp
                245                 250                 255

Val Leu Met Ile Ser Leu Thr Pro Lys Val Thr Cys Val Val Val Asp
            260                 265                 270

Val Ser Glu Asp Asp Pro Asp Val Gln Ile Ser Trp Phe Val Asn Asn
        275                 280                 285

Val Glu Val His Thr Ala Gln Thr Gln Thr His Arg Glu Asp Tyr Asn
    290                 295                 300

Ser Thr Ile Arg Val Val Ser Thr Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ser Pro Ile Glu Arg Thr Ile Ser Lys Ile Lys Gly Leu Val Arg Ala
            340                 345                 350

Pro Gln Val Tyr Ile Leu Pro Pro Pro Ala Glu Gln Leu Ser Arg Lys
        355                 360                 365

Asp Val Ser Leu Thr Cys Leu Val Val Gly Phe Asn Pro Gly Asp Ile
    370                 375                 380

Ser Val Glu Trp Ala Ser Asn Gly His Thr Glu Glu Asn Tyr Lys Asp
385                 390                 395                 400

Thr Ala Pro Val Leu Asp Ser Asp Gly Ser Tyr Phe Ile Tyr Ser Lys
                405                 410                 415
```

```
Leu Asn Met Lys Thr Ser Lys Trp Glu Lys Thr Asp Ser Phe Ser Cys
            420                 425                 430

Asn Val Arg His Glu Gly Leu Lys Asn Tyr Tyr Leu Lys Lys Thr Ile
        435                 440                 445

Ser Arg Ser Pro Gly Lys
    450

<210> SEQ ID NO 22
<211> LENGTH: 1362
<212> TYPE: DNA
<213> ORGANISM: Homo sapiens

<400> SEQUENCE: 22
cagatccagt tggtgcagtc tggacctgag ctgaagaagc ctggagagac agtcaagatc     60
tcctgcaagg cttctggata taccttcaca aactatggaa tgaactgggt gaagcaggct    120
ccaggaaagg gtttaaagtg gatgggctgg ataaacacct acactggaga gccaacatat    180
gctgatgact tcaagggacg gtttgccttc tctttggaaa cctctgccaa cactgcctat    240
ttgcagatca acaacctcag aaatgagggc atggctacat atttctgtgc aagacactat    300
aggtacgcct ggtttcctta ctggggccaa gggactctgg tcactgtctc tgcagccaaa    360
acaacacccc catcagtcta tccactggcc cctgggtgtg gagatacaac tggttcctcc    420
gtgactctgg gatgcctggt caagggctac ttccctgagt cagtgactgt gacttggaac    480
tctggatccc tgtccagcag tgtgcacacc ttcccagctc tcctgcagtc tggactctac    540
actatgagca gctcagtgac tgtcccctcc agcacctggc caagtcagac cgtcacctgc    600
agcgttgctc acccagccag cagcaccacg gtggacaaaa aacttgagcc cagcgggccc    660
atttcaacaa tcaacccctg tcctccatgc aaggagtgtc acaaatgccc agctcctaac    720
ctcgagggtg gaccatccgt cttcatcttc cctccaaata tcaaggatgt actcatgatc    780
tccctgacac ccaaggtcac gtgtgtggtg gtggatgtga gcgaggatga cccagacgtc    840
cagatcagct ggtttgtgaa caacgtggaa gtacacacag ctcagacaca aacccataga    900
gaggattaca acagtactat ccgggtggtc agcaccctcc ccatccagca ccaggactgg    960
atgagtggca aggagttcaa atgcaaggtc aacaacaaag acctcccatc acccatcgag   1020
agaaccatct caaaaattaa agggctagtc agagctccac aagtatacat cttgccgcca   1080
ccagcagagc agttgtccag gaaagatgtc agtctcactt gcctggtcgt gggcttcaac   1140
cctggagaca tcagtgtgga gtgggccagc aatgggcata cagaggagaa ctacaaggac   1200
accgcaccag tcctggactc tgacggttct tacttcatat atagcaagct caatatgaaa   1260
acaagcaagt gggagaaaac agattccttc tcatgcaacg tgagacacga gggtctgaaa   1320
aattactacc tgaagaagac catctcccgg tctccgggta aa                       1362

<210> SEQ ID NO 23
<211> LENGTH: 233
<212> TYPE: PRT
<213> ORGANISM: Artificial sequence
<220> FEATURE:
<223> OTHER INFORMATION: amino acid sequence of mutant TNF

<400> SEQUENCE: 23

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30
```

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
 50                  55                  60

Arg Asp Leu Ser Leu Ile Ser Pro Leu Ala Gln Ala Val Arg Ser Ser
 65                  70                  75                  80

Ser Arg Thr Pro Ser Asp Lys Pro Val Ala His Val Val Ala Asn Pro
            85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160

Val Phe His Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
            210                 215                 220

Gln Val Tyr Phe Gly Ile Ile Ala Leu
225                 230

<210> SEQ ID NO 24
<211> LENGTH: 471
<212> TYPE: DNA
<213> ORGANISM: Artificial sequence
<220> FEATURE:
<223> OTHER INFORMATION: encoding nucleotide sequence of mutant TNF

<400> SEQUENCE: 24
gtcagatcat cttctcgaac cccgagtgac aagcctgtag cccatgttgt agcaaaccct      60
caagctgagg ggcagctcca gtggctgaac cgccgggcca atgccctcct ggccaatggc     120
gtggagctga gagataacca gctggtggtg ccatcagagg gcctgtacct catctactcc     180
caggtcctct tcaagggcca aggctgcccc tccacccatg tgctcctcac ccacaccatc     240
agccgcatcg ccgtcttcca tcagaccaag gtcaacctcc tctctgccat caagagcccc     300
tgccagaggg agacccccga gggggctgag gccaagccct ggtatgagcc catctatctg     360 ggagggtct tccagctgga aagggtgac cgactcagcg ctgagatcaa tcggcccgac     420
tatctcgact tgccgagtc tgggcaggtc tactttggga tcattgccct g              471

<210> SEQ ID NO 25
<211> LENGTH: 15
<212> TYPE: DNA
<213> ORGANISM: Artificial sequence
<220> FEATURE:
<223> OTHER INFORMATION: synthesized nucleotide sequence

<400> SEQUENCE: 25
tacttccaat ccatg                                                       15

```
<210> SEQ ID NO 26
<211> LENGTH: 18
<212> TYPE: DNA
<213> ORGANISM: Artificial sequence
<220> FEATURE:
<223> OTHER INFORMATION: synthesized nucleotide sequence

<400> SEQUENCE: 26 tatccaccttt tactgtta                                                  18

<210> SEQ ID NO 27
<211> LENGTH: 7
<212> TYPE: PRT
<213> ORGANISM: Artificial sequence
<220> FEATURE:
<223> OTHER INFORMATION: synthesized polypeptide sequence

<400> SEQUENCE: 27

Gln Leu Val Val Pro Ser Glu
1               5
```

ANTIBODY FACILITATING PROGRAMMED NECROSIS OF CELLS AND APPLICATION THEREOF

TECHNICAL FIELD

The present invention relates to the field of biomedicine; and in particular, the present invention relates to an anti-TNF monoclonal antibody and use thereof in the treatment of inflammation.

BACKGROUND

Tumor necrosis factor α (TNF) is a multifunctional cytokine secreted by various cells, mainly macrophages and T cells. TNF exerts a variety of biological functions through TNF receptors 1 and 2 (TNFR1 and TNFR2), in which TNFR2 only acts to support TNFR1 in immune cells (1-3).

Many functions of TNF primarily involve three intracellular events: 1) stimulation of transcription factor nuclear factor kappa B (NF-κB), thereby leading to activation of cells and production of cytokines; 2) external pathways that induce apoptosis; and 3) induction of necrosis. These active intracellular signaling pathways share some components but lead to different results: activation of NF-κB leads to secretion of proinflammatory cytokine and survival and activation of cells; apoptosis is a state of cell death, characterized by caspase-3 activation, nuclear breaks, intact cell membranes during early stage, with little or no inflammatory response; however, necrosis is another mechanism of cell death in which no activation of caspase-3 occurs and the integrity of the cell membrane is impaired. Necrosis leads to the release of intracellular substances that stimulate intense immunity and inflammatory responses (4, 5). Under apoptotic conditions, inhibition of caspases may lead to a kind of programmed cell death characterized by necrosis when it occurs, termed "programmed necrosis" (6-11). Because such programmed necrosis is an inflammatory process, it may be clinically associated with diseases such as rheumatoid arthritis, Crohn's disease and psoriasis. However, to date, no factors that trigger programmed necrosis in these diseases have been identified.

Neutralization of TNF by antagonists directly targeting TNF molecules (monoclonal antibodies) or used as pseudoreceptors leads to radical changes in the treatment of inflammatory diseases (12), however complete blocking of TNF function can lead to life-threatening side effects, such as infections and tumors (13). TNF plays an important pathological role in many inflammatory diseases such as rheumatoid arthritis, inflammatory bowel disease, psoriasis and the like. Clinically, it is very effective to treat inflammatory diseases with anti-TNF. Anti-TNF biological agents include: anti-TNF monoclonal antibodies that neutralize TNF, free TNF receptors, and the like. The market for anti-TNF preparations is $15 billion annually.

Despite the above findings, the mechanism by which cells and tissues are destroyed in inflammatory diseases remains unknown: induction of NF-κB is survival-promoting and does not directly lead to cell death—in fact, NF-κB signaling was found to prevent apoptosis in inflammatory bowel disease (14). It is believed that apoptosis is inflammation-inhibiting (15). Programmed necrosis may be a possible mechanism of inflammation and cell/tissue destruction, but lack evidence of clinical relevance in humans. For example, in non-viral inflammatory pathogenesis, it is not known which factor outside the target cell will trigger programmed necrosis (14, 16). Obviously, identification of these factors provides biomarkers for the diagnosis and treatment of many inflammatory diseases.

In sepsis patients, TNF was significantly elevated and positively correlated with the severity of the disease. However, neither traditional TNF-blocking antibodies nor free receptors are effective in treating sepsis, suggesting that other factors may play a key role in synergizing TNF during pathogenicity.

Therefore, there is an urgent need in the art for physical means to regulate and even reverse cell necrosis to treat inflammatory diseases.

SUMMARY OF THE INVENTION

It is an object of the present invention to provide a physical means for regulating and even reversing cell necrosis to treat inflammatory diseases.

In the first aspect, a light chain variable region of an antibody is provided in the present invention, wherein the light chain variable region has Complementarity Determining Region CDR selected from a group consisting of:
  CDR1 as shown in SEQ ID NO: 1,
  CDR2 as shown in SEQ ID NO: 3, and
  CDR3 as shown in SEQ ID NO: 5.

In a preferred embodiment, the light chain variable region has the amino acid sequence as shown in SEQ ID NO: 7.

In the second aspect, a light chain of an antibody is provided in the present invention, wherein the light chain has the light chain variable region according to the first aspect of the invention and a light chain constant region.

In a preferred embodiment, the light chain constant region is shown in SEQ ID NO: 9.

In a preferred embodiment, the amino acid sequence of the light chain is shown in SEQ ID NO: 10.

In a preferred embodiment, the encoding polynucleotide sequence of the light chain is shown in SEQ ID NO: 11.

In the third aspect, a heavy chain variable region of an antibody is provided in the present invention, wherein the heavy chain variable region comprises the following three complementarity determining regions CDRs:
  CDR1 as shown in SEQ ID NO: 12,
  CDR2 as shown in SEQ ID NO: 14, and
  CDR3 as shown in SEQ ID NO: 16.

In a preferred embodiment, the heavy chain variable region has the amino acid sequence as shown in SEQ ID NO: 18.

In the fourth aspect, a heavy chain of an antibody is provided in the present invention, wherein the heavy chain has the heavy chain variable region according to the third aspect of the invention and a heavy chain constant region.

In a preferred embodiment, the heavy chain constant region is shown in SEQ ID NO: 20.

In a preferred embodiment, the amino acid sequence of the heavy chain is shown in SEQ ID NO: 21.

In a preferred embodiment, the encoding polynucleotide sequence of the heavy chain is shown in SEQ ID NO: 22.

In a fifth aspect, the invention provides an antibody having:
  (1) the light chain variable region according to the first aspect of the invention; and/or
  (2) the heavy chain variable region according to the third aspect of the present invention.

In a preferred embodiment, the antibody has: the light chain according to the second aspect of the invention; and/or a heavy chain according to the fourth aspect of the invention.

In the sixth aspect, recombinant protein is provided in the present invention, wherein the recombinant protein comprises:

(i) the sequence of the light chain variable region according to the first aspect of the present invention, the sequence of the light chain according to the second aspect of the present invention, the sequence of the heavy chain variable region according to the third aspect of the present invention, the sequence of the heavy chain according to the fourth aspect, or the sequence of the antibody according to the fifth aspect of the invention; and (ii) an optional tag sequence that assists in expression and/or purification.

In a preferred embodiment, the tag sequence comprises a 6His tag.

In the seventh aspect, an antibody that specifically binds to the sequence QLVVPSE is provided in the present invention.

In the eighth aspect, a polynucleotide is provided in the present invention, wherein it encodes a polypeptide selected from a group consisting of:

(1) the sequence of the light chain variable region according to the first aspect of the present invention, the sequence of the light chain according to the second aspect of the present invention, the sequence of the heavy chain variable region according to the third aspect of the present invention, the sequence of the heavy chain of the fourth aspect, or the sequence of the antibody of the fifth aspect or the seventh aspect according to the present invention; or (2) the recombinant protein according to the sixth aspect of the present invention.

In the ninth aspect, a vector is provided in the present invention, wherein it comprises the polynucleotide according to the eighth aspect of the invention.

In a preferred embodiment, the vectors include: a bacterial plasmid, bacteriophage, yeast plasmid, plant cell virus, mammalian cell virus, such as adenoviruses, retroviruses, or other vectors.

In the tenth aspect, a genetically engineered host cell is provided in the present invention, wherein it comprises the vector according to the ninth aspect of the present invention or has the polynucleotide according to the eighth aspect of the present invention integrated into its genome.

In the eleventh aspect, a pharmaceutical composition is provided in the present invention, wherein it comprises:

(i) the light chain variable region according to the first aspect of the present invention, the light chain according to the second aspect of the present invention, the heavy chain variable region according to the third aspect of the present invention, the heavy chain according to the fourth aspect of the present invention, the antibody according to the fifth aspect or the seventh aspect of the present invention, or the recombinant protein of the sixth aspect of the present invention, and (ii) an optional pharmaceutically acceptable carrier.

In a preferred embodiment, the pharmaceutical composition is an injectable dosage form.

In a preferred embodiment, the pharmaceutical composition is used to prepare a medicament for treating tumor, bacterial or viral infections.

In the twelfth aspect, an inhibitor of the antibody facilitating programmed necrosis of cells is provided in the present invention, wherein the inhibitor of the antibody facilitating programmed necrosis of cells is capable of binding to the antibody according to the fifth aspect or the seventh aspect of the present invention.

In a preferred embodiment, the inhibitor of the antibody facilitating programmed necrosis of cells is a mutant form of TNF which is, compared with the wild type TNF, capable of binding to the antibody according to the fifth aspect or the seventh aspect of the invention instead of TNF receptor.

In a preferred embodiment, the mutant TNF is shown in SEQ ID NO: 23.

In a thirteenth aspect, use of the inhibitor of the antibody facilitating programmed necrosis of cells according to the eleventh aspect of the present invention in the manufacture of a medicament for treating an inflammatory disease is provided.

In a preferred embodiment, the inflammatory disease includes rheumatoid arthritis, Crohn's disease, psoriasis, sepsis.

In the fourteenth aspect, use of a fragment of QLVVPSE or the antibody according to the fifth or seventh aspect of the invention in the manufacture of a test agent for the diagnosis of inflammatory diseases or typing a patient of an inflammatory disease.

In a preferred embodiment, the use is to type a patient.

In the fifteenth aspect, a test kit for diagnosing an inflammatory disease or typing a patient suffering from an inflammatory disease is provided in the present invention, comprising:

a. QLVVPSE fragment or an antibody according to the fifth or seventh aspect of the invention as a standard; and b. instruction on detecting the presence of an anti-TNF autoantibody that specifically binds to QLVVPSE, or an anti-TNF autoantibody that competes with the antibody according to the fifth or seventh aspect of the invention in a sample from a patient using the fragment of QLVVPSE or the antibody according to the fifth or seventh aspect of the invention as a standard.

In the sixteenth aspect, a method for the prognosis of an inflammatory disease is provided in the present invention, comprising detecting the presence of an antibody that competes with the antibody according to the fifth or seventh aspect of the invention for antigen binding site in a body fluid from a patient.

In a preferred embodiment, the bodily fluid comprises blood or synovial fluid.

In a preferred embodiment, the inflammatory disease includes rheumatoid arthritis, Crohn's disease, psoriasis, sepsis.

In the seventeenth aspect, a method for treating an inflammatory disease is provided in the present invention, comprising administering to a patient in need thereof an inhibitor of the antibody facilitating programmed necrosis of cells which is capable of binding to the antibody according to the fifth or the seventh aspect of the invention.

In a preferred embodiment, the inhibitor of the antibody facilitating programmed necrosis of cells is a mutant form of TNF which is, compared with the wild type TNF, capable of binding to the antibody according to the fifth aspect or the seventh aspect of the invention, instead of TNF receptor.

In a preferred embodiment, the mutant TNF is shown in SEQ ID NO: 23.

In a preferred embodiment, the inflammatory disease includes rheumatoid arthritis, Crohn's disease, psoriasis, sepsis.

It should be understood that in the present invention, the technical features specifically mentioned above and below (such as in the Examples) can be combined with each other, thereby constituting a new or preferred technical solution which needs not be individually described.

DESCRIPTION OF DRAWINGS

The patent of application file contains at least one drawing executed in color. Copies of this patent or patent application publication with color drawing(s) will be provided by the Office upon request and payment of the necessary fee.

MODE FOR CARRYING OUT THE INVENTION

Figure 1:
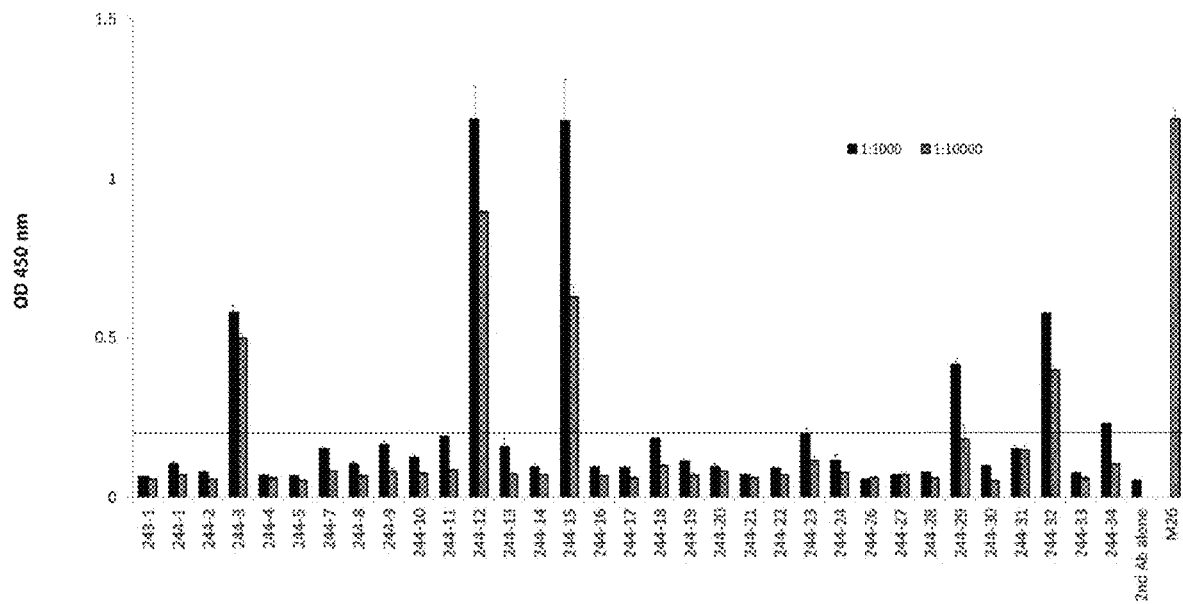
FIG. 1 shows screening of a monoclonal antibody that can bind to TNF from 33 monoclonal antibodies, in which 244-12 was proved to be the strongest for binding TNF by ELISA test.

After extensive and in-depth research, the inventors unexpectedly discovered that antibodies can cause programmed necrosis. In particular, the present inventors found that antibody 244-12 convert TNF-induced apoptosis into programmed necrosis in the presence of TNF. And then it was found that, in some patients with inflammatory diseases, such as arthritis, sepsis, there were similar autoantibodies which can cause programmed necrosis, and conditions of such patients was significantly exacerbated. Therefore, blocking autoantibodies in patients by using a mutant TNF that does not bind to TNFR1 can treat inflammation without causing serious side effects. Based on the above findings, the present invention has been completed.

As used herein, apoptosis or cell apoptosis refers to programmed cell death, that is, death of cells through signaling. It is characterized by atrophy of cells, rupture of nucleus, however, integrity of cell membrane can be maintained. Apoptosis won't cause inflammation, since the cell membrane is intact and apoptotic cells are rapidly phagocytosed by macrophages.

Necrosis or cell necrosis as described herein refers to death of cells due to external forces and is characterized by disruption of cell as well as disruption and incompleteness of cell membrane. When it is in necrosis, a cell releases a lot of inflammatory substances, such as nucleic acid, uric acid, HMGB1 and so on, which will cause inflammation.

As used herein, programmed necrosis or programmed necrosis of cell refers to death of a cell by signaling. It is characterized by disruption of cell as well as disruption and incompleteness of cell membrane. Like the cell necrosis as mentioned above, necrotic cells release many inflammatory substances, such as nucleic acids, uric acid, HMGB1 and the like during programmed necrosis and therefore inflammation will be incurred.

TNF and Functions Thereof

TNF is a multifunctional cytokine secreted mainly by macrophages and T cells. It exerts a variety of biological functions through TNF receptors 1 and 2 (TNFR1 and TNFR2), including stimulation of transcription factor, nuclear factor kappa B (NF-κB); induction of an external pathway for cell apoptosis; and induction of necrosis.

In most cases, stimulation of cells by TNF mainly activates NF-κKB for cell survival. Apoptosis and necrosis will be triggered only when NF-κB pathway is inhibited (24). It was suggested that stimulation of membrane-bound complex I by TNF (25) will initiate activation of NF-κB but do not initiate apoptosis/necrosis. However, if activation of NF-kappa B is arrested, TNF stimulates target cells thereof to form a second complex (Complex II) in cytoplasm, which directs the signaling pathway towards cell death.

At present, all of studies highlight downstream results after TNF-TNFR1 binding. However, no subtle molecular basis has been investigated at the level of TNF-TNFR1 interaction at which different cellular functions may be observed. The general concept is that TNF-TNFR1 binding is sufficient to initiate all of TNF functions, including stimulation of NF-κB and induction of cell death.

Antibody of the Present Invention

Herein, "antibody of the present invention", "monoclonal antibody of the present invention" and "244-12" have the same meaning and refer to an antibody capable of binding to TNF, especially, capable of specifically binding to the sequence QLVVPSE (SEQ ID NO: 27).

The monoclonal antibody of the present invention is a monoclonal antibody that can cause programmed necrosis. The monoclonal antibody can not only bind to TNF but also the formed antigen-antibody complex can further bind to TNF cell membrane surface receptors to promote programmed cell death. Such necrosis can be inhibited by Necrostatin-1.

In addition, the monoclonal antibodies of the invention include anti-TNF antibodies that specifically binds to QLVVPSE (SEQ ID NO: 27), or antibodies that compete with 244-12, and these antibodies also exacerbate the inflammatory response in the presence of TNF, for example, increased TNF.

The present invention includes not only intact monoclonal antibodies, but also immunologically active antibody fragments such as Fab or (Fab')$_2$ fragments; antibody heavy chains; and antibody light chains.

As used herein, the term "heavy chain variable region" is used interchangeably with "VH".

As used herein, the terms "variable region" and "complementarity determining region (CDR)" can be interchangeably used.

As used herein, the terms "light chain variable region" and "VL" can be interchangeably used.

In a specific embodiment, the light chain variable region of the antibody of the invention has a complementarity determining region CDR selected from a group consisting of: CDR1 as shown in SEQ ID NO: 1, encoding nucleotide sequence of which is shown in SEQ ID NO: 2; CDR2 as shown in SEQ ID NO: 3, encoding nucleotide sequence of which is shown in SEQ ID NO: 4; and CDR3 as shown in SEQ ID NO: 5, encoding nucleotide sequence of which is shown in SEQ ID NO: 6.

In a preferred embodiment, the amino acid sequence of the light chain variable region is shown in SEQ ID NO: 7, and the encoding nucleotide sequence thereof is shown in SEQ ID NO: 8.

In a preferred embodiment of the invention, the light chain of the antibody comprises the above light chain variable region and light chain constant region.

In a preferred embodiment, the constant region of the light chain is shown in SEQ ID NO: 9.

In a preferred embodiment, the amino acid sequence of the light chain is shown in SEQ ID NO: 10.

In a preferred embodiment, the encoding polynucleotide sequence of the light chain is shown in SEQ ID NO: 11.

In a specific embodiment, the heavy chain variable region of the antibody of the invention comprises the following three complementarity determining regions CDRs: CDR1 as shown in SEQ ID NO: 12, encoding nucleotide sequence of which is shown in SEQ ID NO: 13; CDR2 as shown in SEQ ID NO: 14, encoding nucleotide sequence of which is shown in SEQ ID NO: 15; and CDR3 as shown in SEQ ID NO: 16, encoding nucleotide sequence of which is shown in SEQ ID NO: 17.

In a preferred embodiment, the heavy chain variable region has the amino acid sequence as shown in SEQ ID NO: 18, and the encoding nucleotide sequence thereof is shown in SEQ ID NO: 19.

In a specific embodiment, the heavy chain of the antibody of the invention comprises the heavy chain variable region and heavy chain constant region as described above.

In a preferred embodiment, the heavy chain constant region is shown in SEQ ID NO: 20.

In a preferred embodiment, the amino acid sequence of the heavy chain is shown in SEQ ID NO: 21.

In a preferred embodiment, the encoding polynucleotide sequence of the heavy chain is shown in SEQ ID NO: 22.

In a specific embodiment, the antibody of the present invention comprises:
(1) light chain variable region as described above; and/or
(2) heavy chain variable region as described above.

In a preferred embodiment, the antibody comprises: the light chain as shown in SEQ ID NO: 10; and/or the heavy chain as shown in SEQ ID NO: 21.

Based on the antibodies described above, a recombinant protein and encoding polynucleotide thereof are provided in the present invention, the recombinant protein comprising:
(i) the sequence of the light chain variable region as described above, the sequence of the light chain as described above, the sequence of the heavy chain variable region as described above, the sequence of the heavy chain as described above, or the sequence of the antibody as described above; and
(ii) optional tag sequences assisting in expression and/or purification.

In a preferred embodiment, the tag sequence includes 6His tag.

Based on the recombinant protein described above, a vector is provided in the present invention, comprising the encoding polynucleotide of the recombinant protein.

In another preferred embodiment, the vector includes a bacterial plasmid, a bacteriophage, a yeast plasmid, a plant cell virus, a mammalian cell virus, such as an adenovirus, a retrovirus, or other vectors.

In a further embodiment, a genetically engineered host cell is provided in the invention, comprising the vector as described above or having the encoding polynucleotide of the recombinant protein integrated into the genome.

Figure 7:
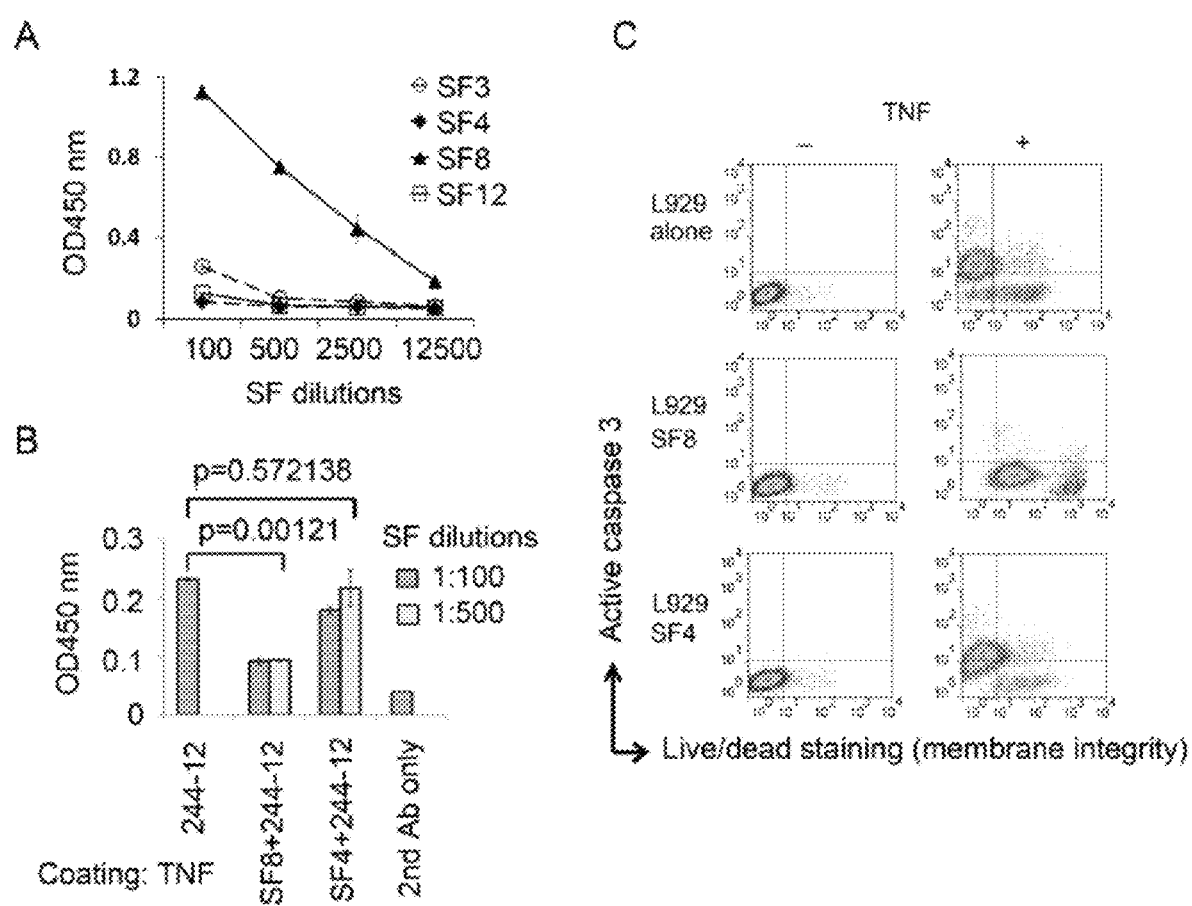
FIG. 7A shows the presence of anti-TNF autoantibodies in synovial fluid of some arthritic patients.
FIG. 7B shows that autoantibodies compete with 244-12 for TNF binding sites.
FIG. 7C shows that SF8 synovial fluid causes programmed necrosis in the presence of TNF.

By analyzing serum samples from normal people, patients of arthritis, dead patients of sepsis and survival patients of sepsis, the present inventors found that there are similar autoantibodies that will cause programmed cell necrosis present in the human body. Moreover, such autoantibodies competitively inhibit binding of monoclonal antibody 244-12 of the present invention to TNF. FIG. 7 shows a representative patient (in the figure, SF8 represents the patient, other similar patients exhibit the same result; SF4 represents negative control); and these patients' serum or synovial fluid together with TNF can cause cell necrosis (FIG. 7). The inventors found that, there were autoantibodies against full-length TNF protein in some patients, and such autoantibodies did not cause programmed cell necrosis if they did not compete with 244-12 for binding sites. These autoantibodies that can compete with 244-12 for binding sites have a good correlation with the severity of the disease, which may be one of the reasons for the increased inflammation.

Accordingly, in another aspect, a method for detecting anti-TNF autoantibodies that can cause programmed necrosis is provided in the present invention. The method includes detecting the presence of an anti-TNF autoantibody that specifically binds QLVVPSE (SEQ ID NO: 27) in a patient; or detecting the presence of an anti-TNF autoantibody which can compete with the monoclonal antibody 244-12 of the invention in a patient; and if an anti-TNF autoantibody which specifically binds to QLVVPSE (SEQ ID NO: 27) is present in a patient or if the detected autoantibody can compete with 244-12, then these autoantibodies may exacerbate the inflammatory response in the presence of TNF, for example at increased levels. A patient can be typed after detecting whether an anti-TNF autoantibody which specifically binds to QLVVPSE (SEQ ID NO: 27) is present in the patient or whether an anti-TNF autoantibody which competes with the monoclonal antibody 244-12 of the invention is present, as for example, a patient with good prognosis or poor prognosis.

In view of the teachings of the present invention, a skilled person knows that the fragment of QLVVPSE (SEQ ID NO:

27), or the antibodies of the invention, can be used as a standard to detect the presence of anti-TNF autoantibodies which specifically bind to QLVVPSE (SEQ ID NO: 27) or anti-TNF autoantibodies which compete with antibodies of the invention in a patient's sample; and then whether the patient has an inflammatory disease can be diagnosed and a patient with an inflammatory disease can be typed.

Moreover, a test kit for diagnosing an inflammatory disease or typing a patient suffering from an inflammatory disease is provided in the present invention, comprising:

a. a fragment of QLVVPSE (SEQ ID NO: 27) or an antibody of the present invention as a standard; and b. an instruction manual regarding detecting the presence of an anti-TNF autoantibody which specifically binds to QLVVPSE (SEQ ID NO: 27) or an anti-TNF autoantibody which competes with an antibody of the invention in a patient's sample by using the fragment of QLVVPSE (SEQ ID NO: 27) or the antibody of the present invention as a standard.

In the present invention, a method for the prognosis of an inflammatory disease is further provided, including detecting the presence of an antibody in a patient's body fluid which competes with the antibody of the invention for antigen binding sites. In a specific embodiment, the body fluid includes blood or synovial fluid. In a preferred embodiment, the inflammatory diseases include rheumatoid arthritis, Crohn's disease, psoriasis, sepsis.

Based on the above findings, the antagonist, inhibitor or neutralizing agent of the antibody of the present invention can treat, alleviate and relieve inflammatory diseases, such as rheumatoid arthritis, Crohn's disease and psoriasis. For example, in a particular embodiment, a mutant TNF capable of binding to 244-12 or a similar antibody thereof, such as a similar antibody in the body of a patient with an inflammatory disease, while not binding to TNF receptor, or an antibody specific to the antibody of the invention, 244-12 or a similar antibody thereof can reverse 244-12-induced necrosis.

In the present invention, a method for treating an inflammatory disease is also provided, including administering to a patient in need thereof an inhibitor of the antibody facilitating necrosis of cells, wherein the inhibitor of the antibody facilitating necrosis of cells can bind to the antibody of the present invention. In a preferred embodiment, the inhibitor of the antibody facilitating necrosis of cells is an antibody specific to antibody 244-12 of the invention or a similar antibody thereof.

In a preferred embodiment, the inhibitor of the antibody facilitating necrosis of cells is a mutant TNF which, compared with a wild-type TNF, is capable of binding to the antibody facilitating necrosis of cells but not to TNF receptor.

In a preferred embodiment, the amino acid sequence of the mutant TNF is shown in SEQ ID NO: 23 (mutation: S162F, Y163H).

In addition, since the antibody of the present invention, 244-12, is capable of inducing programmed necrosis of cells in the presence of TNF and such necrosis will cause inflammation and recruit immune cells to elicit specific immune responses, the antibody of the present invention can be used to treat tumors or viral or bacterial infections.

Based on the above findings, a pharmaceutical composition is also provided in the present invention, comprising:

(i) a light chain variable region as described above, a light chain as described above, a heavy chain variable region as described above, a heavy chain as described above, an antibody described above, or a recombinant protein as described above; and (ii) an optional pharmaceutically acceptable carrier.

Advantages of the Present Invention

1. The inventors firstly discovered that antibodies can induce programmed necrosis of cells;
2. The results of the present inventors have significant clinical significance;
3. The antibody of the present invention can be used to detect an antibody which can compete with the antibody of the present invention for antigen binding sites, and eliminating these autoantibodies may treat, alleviate or reduce the inflammatory response;
4. Since the antibodies of the present invention and TNF can induce programmed necrosis of cells and such necrosis can cause inflammation and recruit immune cells to elicit specific immune responses, the antibody of the present invention can be used to treat tumors or viral or bacterial infections.

The invention will be further illustrated with reference to the following specific examples. It is to be understood that these examples are only intended to illustrate the invention, but not to limit the scope of the invention. For the experimental methods in the following examples without particular conditions, they are performed under routine conditions, such as conditions described in Sambrook et al., Molecular Cloning: A Laboratory Manual, New York: Cold Spring Harbor Laboratory Press, 1989, or as instructed by the manufacturer. Unless otherwise stated, the percentages and parts are percentages by weight and parts by weight.

Material and Methods

Patient

Patients were recruited through the rheumatology clinics at the Nuffield Orthopaedic Centre Oxford and all samples were stored at −80° C. until analysis. Synovial fluid was aspirated from the knee joints of patients with inflammatory disease as part of therapeutic arthrocentesis. Rheumatoid arthritis was defined according to the 1987 American College of Rheumatology or 2010 ACR/EULAR classification criteria; other inflammatory arthropathies were diagnosed on the basis of clinical and radiographic criteria. All rheumatoid patients were seropositive for rheumatoid factor and had moderate disease activity. Samples and/or data obtained were collected with informed donor consent in full compliance with national and institutional ethical requirements (COREC number COREC06/Q1606/139).

Cell Lines, TNF and Peptides

Mouse fibrosarcoma L929 cells and human lymphocytes Jurkat A3 cells were purchased from American Type Culture Collection (ATCC, Manassas, Va.). Human C28I2 chondrocytes were provided by Dr. Mary B. Goldring. Human SaOs-2 osteoblasts were purchased from Sigma. TNF was purchased from Immunotools (Germany).

Apoptosis and Necrosis Assay

Cells were incubated overnight (or for times as indicated in the figures) in the presence of TNF□ (Immunotools, Friesoythe, Germany) or TNF peptides with or without 20 µM z-VAD-FMK (R & D Systems, Minneapolis, Minn.) or 20 µM Necrotatin-1 (PeproTech, Rocky Hill, N.J.). In some experiments, TNF□ and □ cells were co-cultured with monoclonal antibodies or synovial fluids at the indicated concentration. The cells were stained with live/dead cell staining kits (Invitrogen, Paisley, UK) instructed by the manufacturer's manual and fixed using cytofix/cytoperm fixation/permeabilization solution kits (BD Pharmingen, Oxford, UK). This was followed by intracellular staining with FITC-conjugated anti-caspase-3 antibody (Cell Signaling Technology, Danvers, Mass., USA). Cells were acquired on a CyAn flow cytometer (Beckman Coulter, Fullerton, Calif.) and data were analyzed using Flowjo (Tree Star Inc. Ashland, Oreg.).

TNF Cytotoxicity Assay

Adherent L929 cells (100 µl, 4×10$^5$/ml) were incubated with TNF in the presence or absence of actinomycin D (2-10 µg/ml) (Sigma) overnight at 37° C., 5% $CO_2$. After aspiration of all the supernatant, 50 µl of 0.05% crystal violet was added to each well to stain the viable cells. After rinsing off crystal violet, the viability of the adherent cells was determined.

NF-κB Assay

Jurkat A3 cells which were treated with TNF or its peptide at the indicated time points (FIGS. 1B and 2A) were collected and lysed with a RIPA lysis buffer (Cell Signaling Technology, Danvers, Mass., USA) containing protease cocktail inhibitor (Sigma). Cell extracts were analyzed by SDS-PAGE and then blotted to a nitrocellulose membrane (Amersham Life Science, England) and then probed by IκB antibody (Cell Signaling Technology, Danvers, Mass., USA) using chemiluminescence.

Transmission Electron Microscopy

In some experiments, after the incubation of cells with peptides, the cells were processed for examination by transmission electron microscopy (a service was provided by Oxford Brooks University). Briefly, the cells were fixed in 2.5% glutaraldehyde in PBS and post-fixed in 1% osmium tetroxide. After dehydration in a graded ethanol series, the specimens were embedded in TAAB 'Premix' epoxy resin (medium hardness). Sections of approx 60 nm thickness were cut on an RMC PT-PC ultramicrotome on a diamond knife, collected on 200 mesh uncoated (cleaned) copper grids, stained with uranyl acetate and lead citrate and examined under a Hitachi H-7650 TEM at 120 Kv.

Nuclear DNA Fragmentation

Alternatively, some of the cells were stained with DAPI (Vector Laboratories, Burlingame, Calif., USA) in addition to using Live/Dead staining kits and anti-caspase-3 antibody (BD). They were then observed under a fluorescent microscope.

THP-1-X Blue NF-κB Assay

THP-1-XBlue Nf-κB reporter cells were obtained from invivoGen (San Diego, Calif. 92121). Cells were incubated with TNF-α peptides at the indicated concentrations. LPS and soluble TNF-α were the positive controls. Cell culture supernatants were collected and NF-κB was measured following the provider's instructions.

ELISA

Screening Monoclonal Antibodies/Inhibition Assay

ELISA plates were coated with TNF or mTNF-HA at 2 µg/ml overnight at 4° C. or 2 hours at 37° C. followed by incubating with monoclonal antibodies at 37° C. for 1 hour. A second antibody conjugated with HRP was used to detect the reaction. For the inhibition assay, TNFR1 or synovial fluids were added together with monoclonal antibodies.

Binding of TNFR1 by TNF

The binding of TNFR1 with TNF was tested by an ELISA assay as follows: an ELISA plate was coated overnight at 4° C. or 2 hours at 37° C. with 1.5 µg/ml TNF or mTNFHA. After incubation of TNFR1 (1 µg/ml) for two hours at 37° C. followed by another two hour's incubation with anti-TNFR1 or anti-HA antibodies, a second anti-mouse IgG1 antibody conjugated with HRP was added for 30 minutes and this was followed by adding its substrates for detection. The colour was developed and measured at OD 450 nm by a Wallace Victor2 1420 multi-label counter (PerkinElmer, Massachusetts, Mass., USA).

L929 Cells Immunofluorescence Microscopy

TNF at 20 ng/ml was incubated with mAbs M26 or 244-12 at 2 µg/ml at room temperature for 1 hour. The mixtures of TNF/M26 or TNF/244-12 were further incubated for 15 min on ice with L929 cells grown on cover slips. The cells were fixed with 4% paraformaldehyde (in PBS) for 10 min, blocked in a phosphate-buffer containing 0.5% BSA and 0.1% cold water fish-gelatin for 15 min and subsequently incubated with rabbit anti-TNFR1 antibodies (Abcam) for 1 hour. The cells were extensively washed in PBS and then incubated with the relevant secondary antibodies, which were conjugated with Alexa Fluor 488 or Alexa Fluor 568 21 (Invitrogen). PBS-washed specimens were then mounted in Gelvatol/DABCO (Sigma-Aldrich). DNA was counterstained with DAPI (Sigma-Aldrich). All samples were analyzed by fluorescent microscopy using a Nikon Eclipse 80i at 60×. Images were acquired with NIS-Elements AR3.0 software using a Hamamatsu camera.

EXAMPLE

Example 1

Preparation of Monoclonal Antibody 244-12 and Identification of its Binding Epitopes The inventors prepared 33 monoclonal antibodies by conventional methods and examined the binding of the prepared monoclonal antibodies to TNF, wherein it was demonstrated through ELISA that the monoclonal antibody 244-12 bound TNF the strongest.

Subsequently, the inventors identified the binding epitope of monoclonal antibody 244-12 as QLVVPSE.

Example 2

Conversion of TNF-Related Apoptosis to Programmed Necrosis by Monoclonal Antibody 244-12

The inventors studied the effect of monoclonal antibody (mAb) 244-12 on TNF function.

Figure 2:
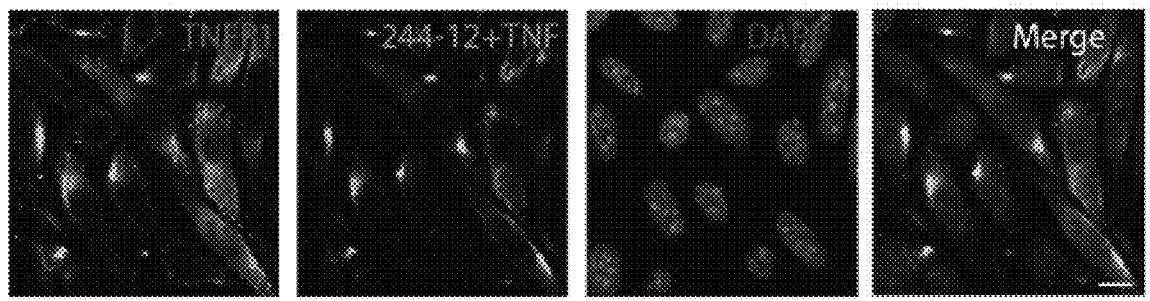
FIG. 2 shows that the binding of antibody 244-12 of the present invention to TNF does not affect the binding of TNF to cell surface receptors, where "Merge" means combined and "alone" means only antibody 244-12.
Figure 2:
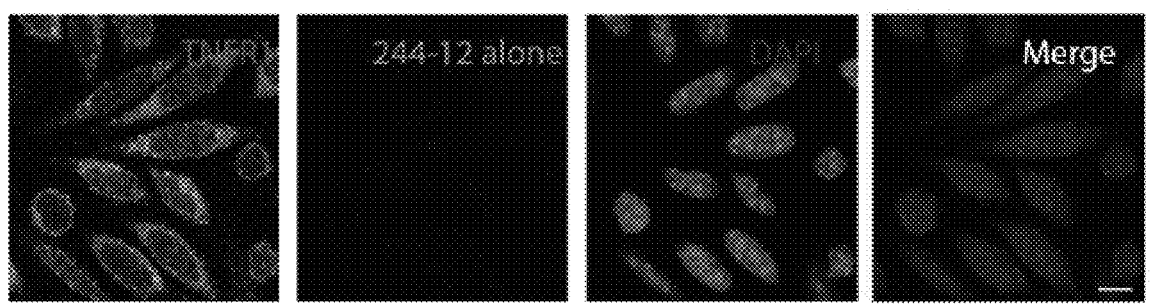

Firstly, the confocal microscope photograph in FIG. 2 shows that the monoclonal antibody 244-12 binds to TNF and does not affect the binding of TNF to TNF receptors. Under confocal microscopy, TNF receptors were stained red, and 244-12 was stained green. Wherein, the above panel shows that green and red overlapped (yellow) in the presence of TNF, indicating that 244-12 overlapping with TNF and TNF receptors; and the bottom panel shows that in the absence of TNF, there was only red indicating that 244-12 can not directly bind to cell surface.

Figure 3:
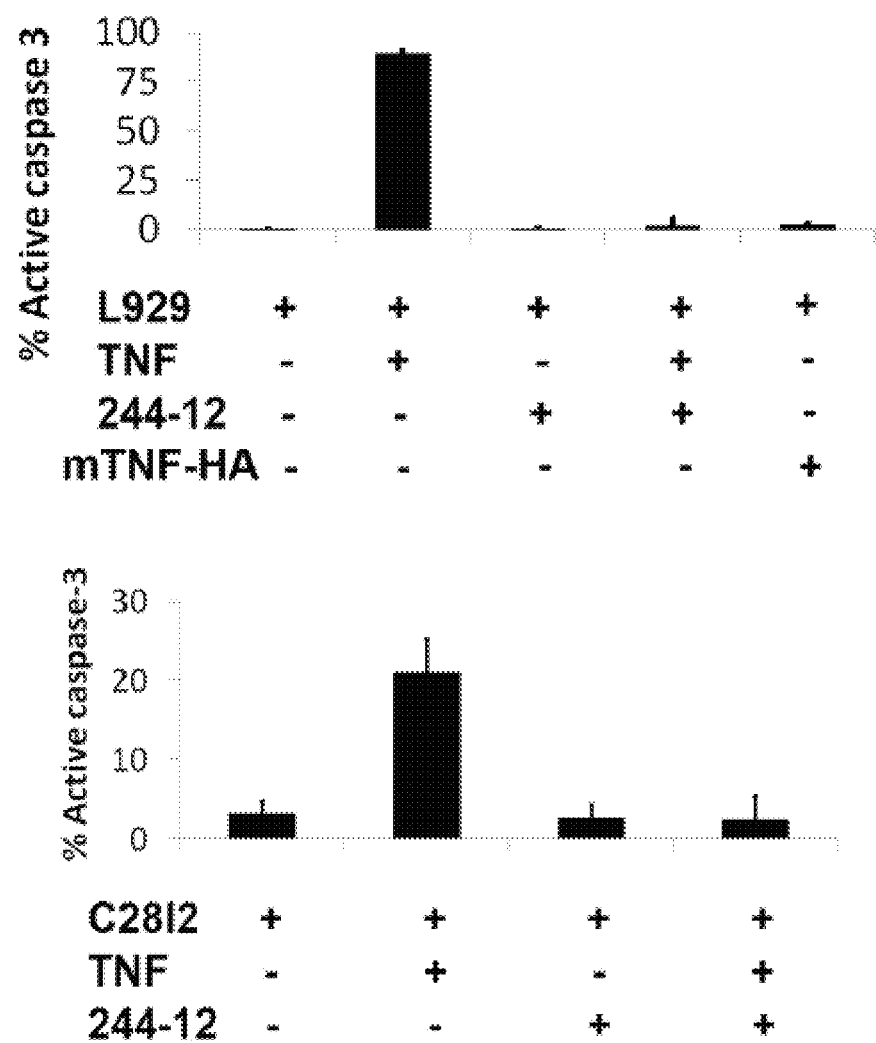
FIG. 3 shows that antibody 244-12 of the invention blocks TNF-induced apoptosis (i.e, expression of active caspase-3) in both cell lines, in which the upper panel shows L929 cells (mouse fibroblast cells) and the bottom panel shows C28I2 cells (chondrocytes)

Subsequently, the inventors observed that stimulation of L929 cells by TNF induced apoptosis (active caspase-3 expression), whereas apoptosis was inhibited (active caspase-3 inhibition) when mAb 244-12 was added. FIG. 3 shows that monoclonal antibody 244-12 blocked TNF-induced apoptosis in both cell lines, L929 cells (mouse fibroblastoma cells, above panel) and C28I2 cells (chondrocytes, bottom panel) (i.e, Active caspase-3 expression).

However, when the monoclonal antibody 244-12 was added to TNF and L929 cells, it was unexpectedly found that apoptosis was inhibited, while the necrosis of cells occurred.

Figure 4:
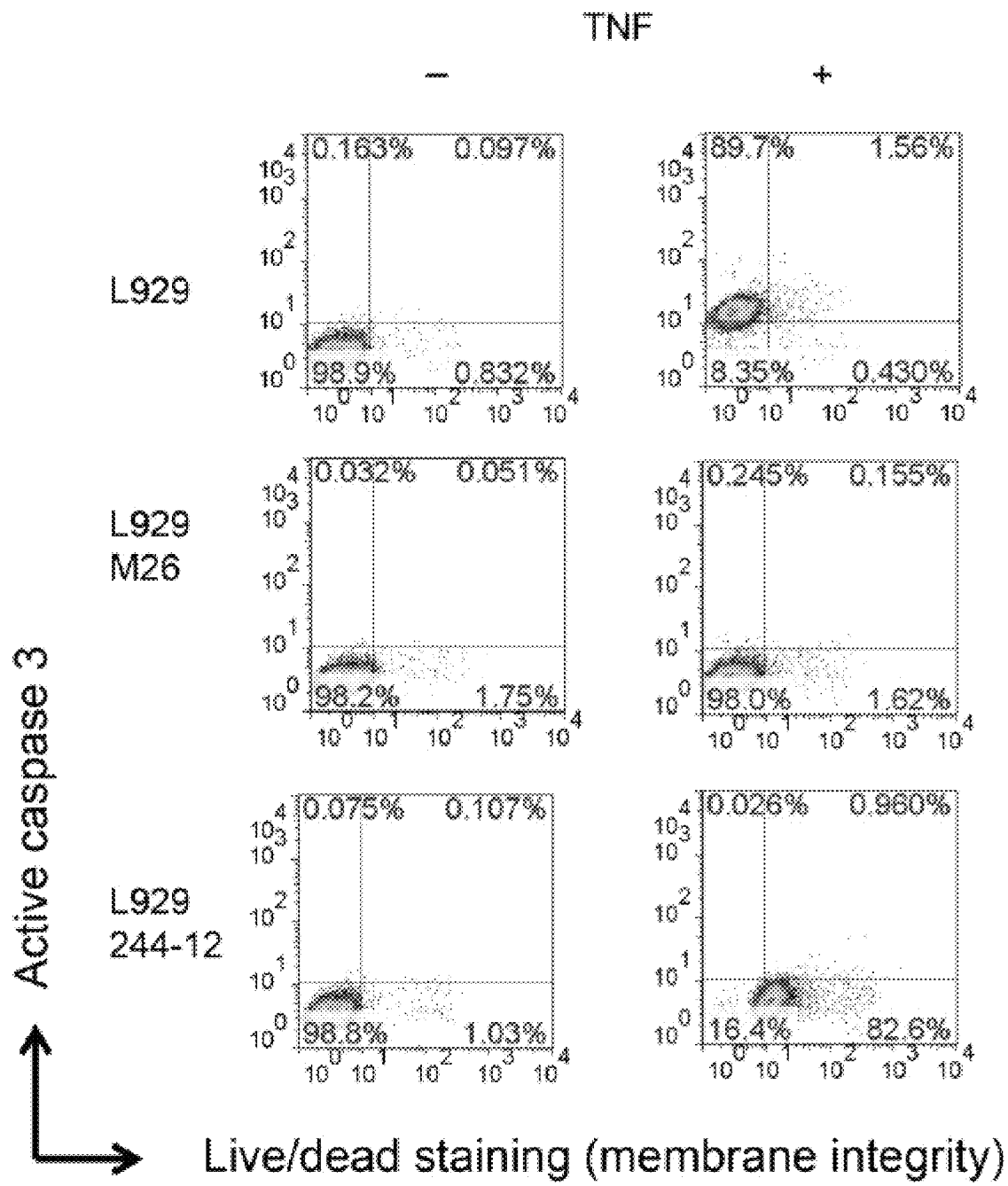
FIG. 4 shows that the binding of antibody 244-12 of the invention and TNF will result in necrosis of L929 cell, in which the vertical axis shows cell apoptosis (active caspase-3) and the horizontal axis shows cell necrosis (destruction of integrity of cell membrane). Wherein, it is shown that TNF induced cell apoptosis (the right of upper panel); when M26 control antibody was added (to block TNF binding to receptor), L929 cell survived (the right of the middle panel); and when 244-12 was added with TNF, it shows necrosis of L929 cell (the right of the bottom panel)

FIG. 4 shows that antibodies 244-12 and TNF induced L929 cell necrosis. Among them, TNF induced apoptosis (right in above panel); after control antibody M26 (blocking TNF binding receptor) was added, L929 cells survived (right in middle); after 244-12 and TNF were added, necrosis of L929 cells occurred (right in bottom panel).

Figure 5:
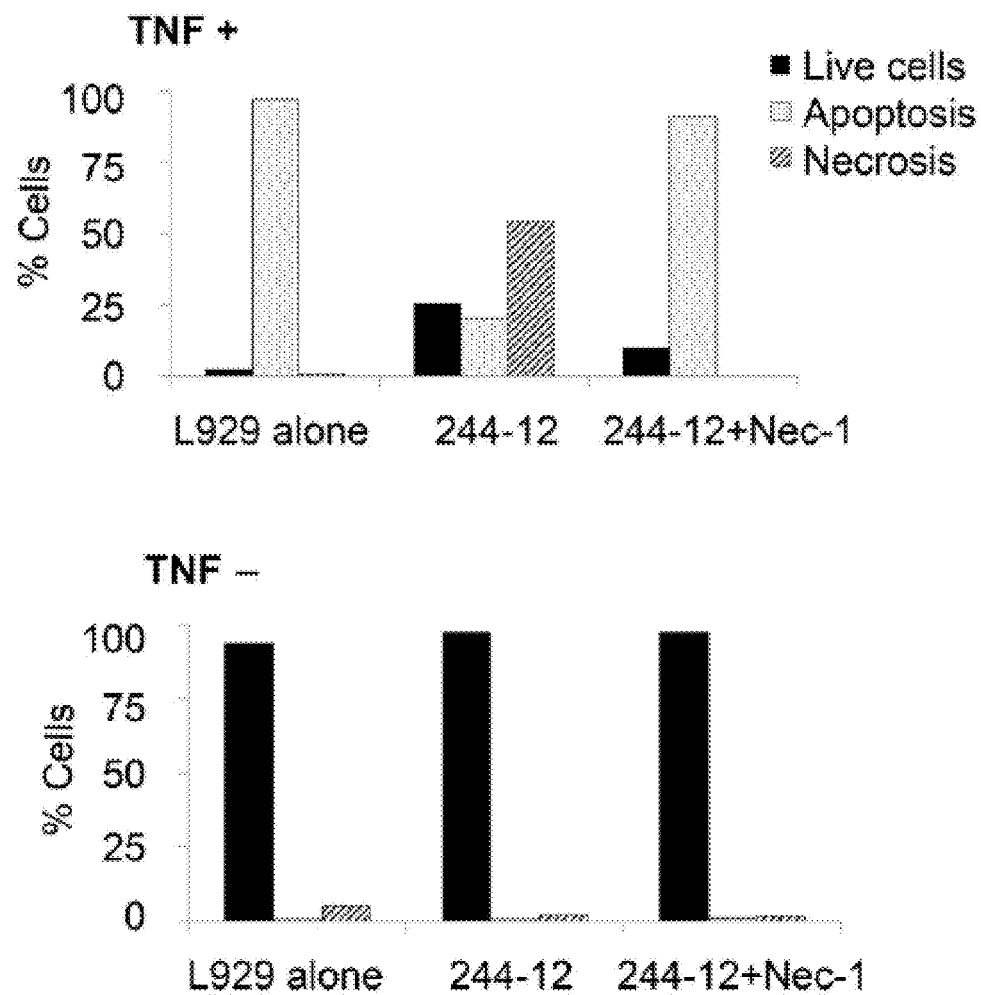
FIG. 5 shows that necrosis caused by antibody 244-12 of the present invention+TNF can be inhibited by Nec-1, in which after adding Nec-1 in 244-12+TNF (the right of the upper panel), cell necrosis transformed into apoptosis, indicating that cell necrosis is through signal transduction, namely programmed necrosis.

Upon further studying the inventor demonstrated that necrosis induced by 244-12+TNF is signal-transduced. FIG. 5 shows that necrosis caused by the antibody 244-12 of the present invention+TNF can be inhibited by Nec-1. Among them, after adding Nec-1 into 244-12+TNF, cell necrosis was conversed into apoptosis (right of above panel), suggesting that cell necrosis is signal-transduced, namely programmed necrosis.

Example 3

Autoantibodies in Synovial Fluid of Patients with Rheumatoid Arthritis Trigger Programmed Necrosis We unexpectedly found that there was a high level of antibodies in synovial fluid of some patients with untreated rheumatoid arthritis or osteoarthritis (FIG. 7A). These antibodies can compete with 244-12 for the antigen binding site (FIG. 7B). These antibody-containing synovial fluids were able to cause programmed necrosis of cells (FIG. 7C).

FIG. 7A shows the presence of anti-TNF autoantibodies in synovial fluid of some arthritic patients. Synovial fluid of the patient SF8 contained high levels of autoantibodies. 7B shows that autoantibodies compete with 244-12 for TNF binding sites. When SF8 synovial fluid was added in a binding assay of 244-12 to TNF (ELISA), binding of 244-12 to TNF was inhibited. 7C shows that SF8 synovial fluid causes programmed necrosis in the presence of TNF. TNF causes apoptosis in L929 cells (right in the upper panel). When SF8 synovial fluid was added, the cells conversed into programmed necrosis (right in the middle panel). The control synovial fluid SF4 did not cause necrosis (right in the bottom panel).

Figure 8:
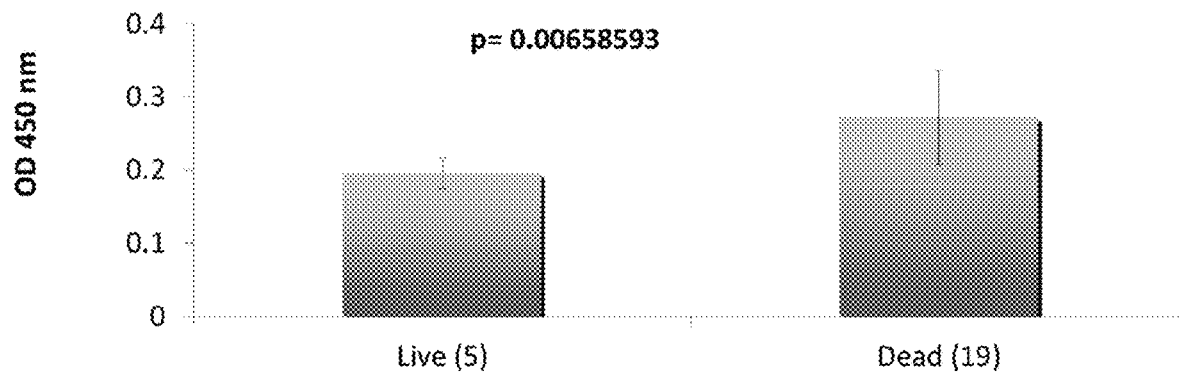
FIG. 8 shows the average level of antibodies that compete with the antibody 244-12 of the invention in binding antigen binding sites in healed patients with sepsis (5) and patients died of sepsis (19). The difference between the two sides is very significant. P<0.01.

The inventors observed another 24 sepsis patients, wherein 14 patients were detected as having antibodies competing with 244-12 for antigen binding site, and the other 10 patients did not contain similar antibodies. The 14 patients with antibodies competing with 244-12 for antigen binding site were well-nourished and treated, however all of them died. Five of the other 10 patients died and another 5 were discharged after 2-3 weeks (results can be found in Table 1). Antibody levels in the dead patients were significantly higher than that in the healed group (p<0.01) (FIG. 8).

Example 5

Expression and Purification of Human TNF-α Mutants in E. coli

1. Cloning of TNFa Mutant S86F/Y87H

Figure 9:
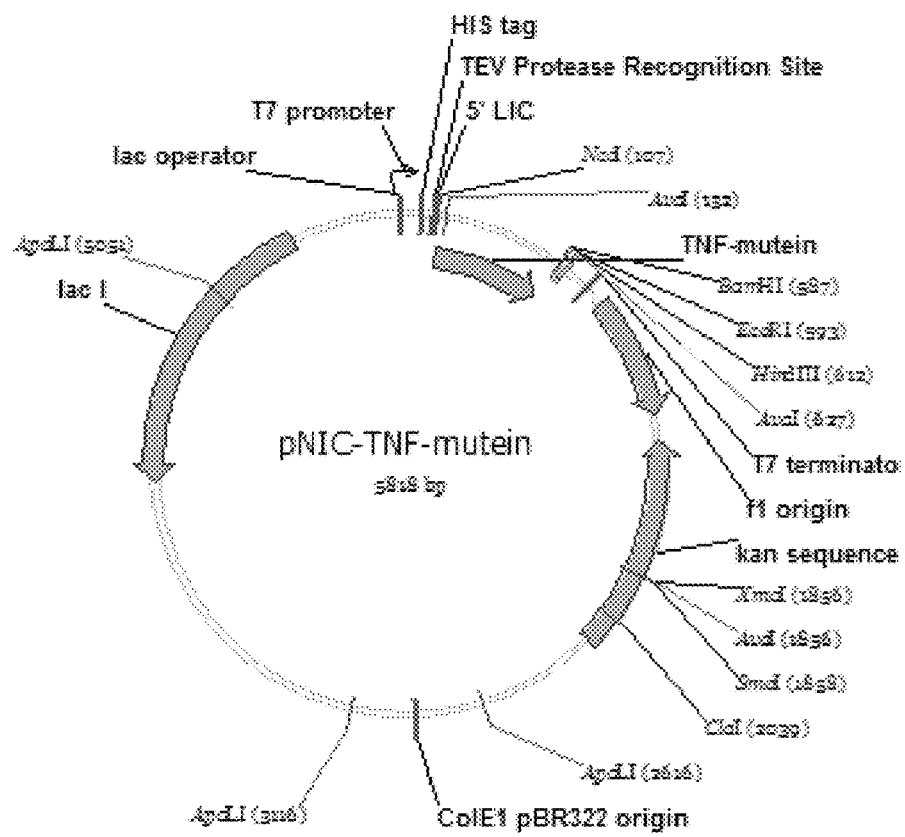
FIG. 9 is a schematic diagram of pNIC28Bsa4 vector showing the important components that are relevant to expression of clones.

The encoding DNA sequence of the mutant was designed based on the amino acid sequence (SEQ ID NO: 24). To facilitate cloning, TACTTCCAATCCATG (SEQ ID NO: 25) was added at the 5' end of the TNF mutant DNA and TATCCACCTTTACTGTTA (SEQ ID NO: 26) sequence was added at the 3' end. The above DNAs were artificially synthesized by GeneArt and then treated with T4 DNA polymerase and dCTP for 30 minutes. pNIC28Bsa4 vector was a gift from Structural Biology Laboratory, University of Oxford, and the important components in the vector which are relevant to the expression of clones are shown in FIG. 9. pNIC28Bsa4 was digested with BsaI for 1 hour and then the linearized vector was separated on 1% agarose gel electrophoresis and treated with T4 DNA polymerase and dGTP for 30 minutes. After both of T4 DNA Polymerase-treated products were mixed, they were transformed into DN5α competent cells and plated, and the single colonies were picked for culture. Positive colonies were identified through bacterial PCR.

2. Expression of TNFa Mutant S86F/Y87H

Plasmid DNAs were extracted from the positive colonies and transformed into E. coli BL21 (DE3). Single colonies were picked and inoculated into LB medium and cultured overnight at 37° C. The culture was diluted at 1:100 with LB medium overnight, and shaken and cultured at 37° C. to OD600=1.0, the culture was cooled to 18° C. and 0.2 mM of IPTG was added for induction of protein expression. After shaken at 18° C. for another 16 hours, the cells were centrifuged at 4000 rpm and the cells were harvested, and resuspended in Tis-HCL, 250 mM NaCl, and 5 mM Imidazole, at pH 8.0 (5 ml buffer per gram of wet bacteria).

3. Purification of TNFa Mutant S86F/Y87H

Cells were sonication-lysed and the supernatant containing the protein of interest was collected by centrifugation at 15,000 rpm and passed through a Ni-NTA column (the protein obtained per liter of the bacterial culture was purified with a 1 ml Ni-NTA column). Single-stranded overlapping peptides with his-tag can be bound to the column and extensively washed (50 times the volume of Ni-NTA column of buffer was used, washing solution=Tis-HCL, 250 mM NaCl, pH 8.0, 15 mM imidazole, pH 8.0) to remove impurity proteins, and TNFa mutant S86F/Y87H was eluted with 5 times the volume of Ni-NTA column (Tis-HCL, 100 mM NaCl, 300 mM imidazole, pH 8.0 with imidazole in elution buffer).

4. Buffer Replacement to PBS after TNFa Mutant S86F/Y87H was Purified by Ni-NTA

PD10 column was equilibrated with PBS, and 2.5 ml of Ni-NTA purified protein was added. After the protein solution completely entered the PD10 column, 3.5 ml of PBS was added to elute TNFa mutant in PBS.

Example 5

Mutant TNF Reverses Programmed Necrosis

Figure 6A:
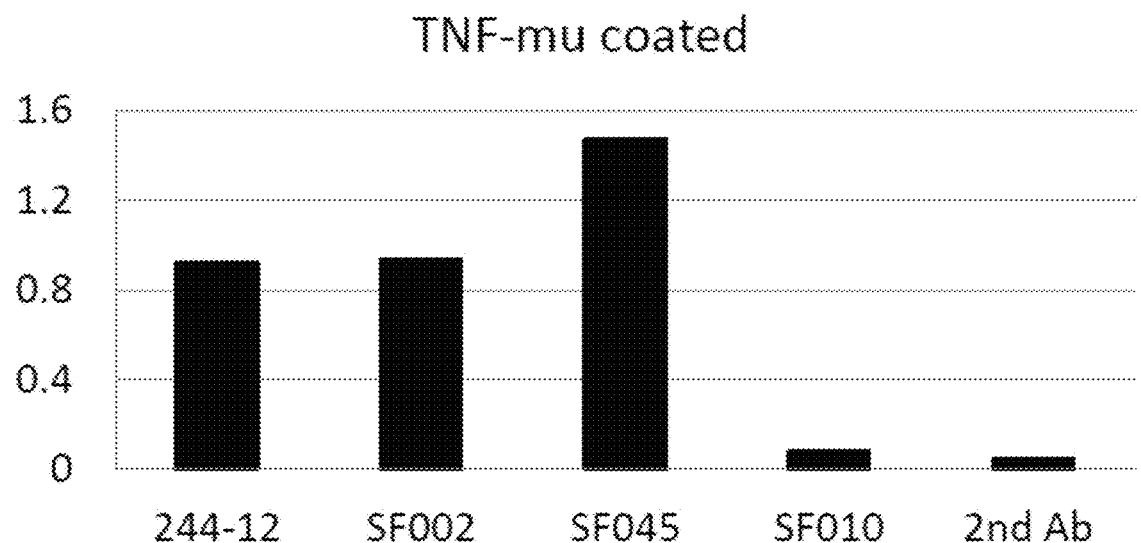
FIG. 6, wherein 6A shows that the mutated TNF (TNF-mu) is capable of binding to antibody 244-12 of the present invention and antibody in synovial fluid of arthritic patients (SF002 and SF045); 6B show that the mutated TNF (TNF-mu) can reverse programmed necrosis caused by TNF+mAb 244-12; first panel from the left: L929 cells: live cells– 93.1% (lower left quadrant); second panel from the left: TNF alone: apoptosis–78.1% (upper left quadrant); third panel from the left: TNF+244-12: necrosis of cell–34.9% (lower right quadrant); fourth panel from the left: TNF+244-12+TNF-mu: reverse to apoptosis–71.3% (lower left quadrant)
Figure 6B:
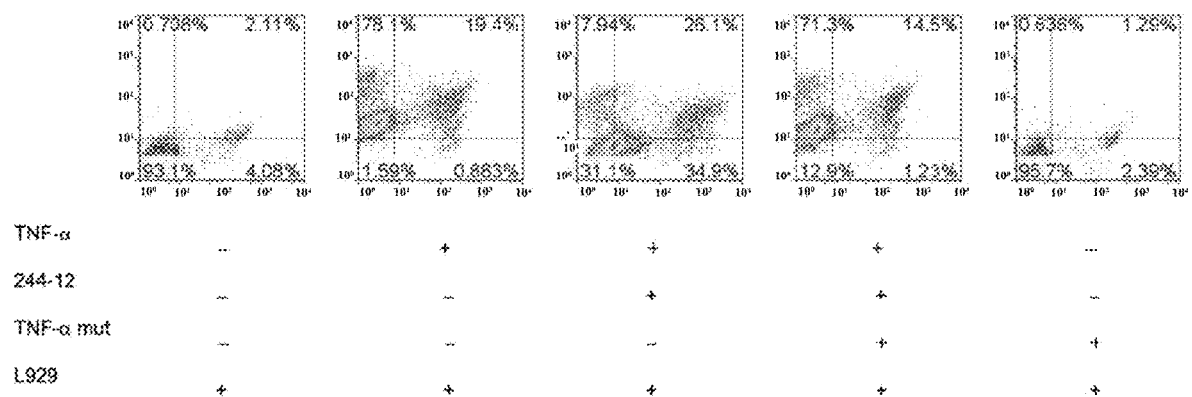

The inventors found that mutant TNF (TNF-mu) is capable of binding to 244-12 and antibodies in synovial fluid (as shown in FIG. 6A); and mutant TNF (TNF-mu) can reverses programmed necrosis (as shown in FIG. 6B).

Example 6

The present inventors further studied antibodies that specifically bind to other TNF molecules and fragments thereof and found that these antibodies exhibited no effects on the conversion of TNF-related apoptosis to programmed necrosis;

In addition, the inventors performing screening experiments by using full-length TNF and found that only antibodies that specifically bind to QLVVPSE (SEQ ID NO: 27) have the effect of converting TNF-related apoptosis into programmed necrosis.

Discussion

Based on our findings, we proposed a new therapeutic strategy for inflammation. The mechanism of programmed necrosis involves autoantibodies and TNF. Programmed necrosis is one of the causes of inflammation. One of the current treatment strategies for inflammatory diseases is to block TNF by inhibiting TNF. This strategy is effective at inhibiting inflammation, however may lead to life-threatening side effects, such as TB or lymphoma. The present inventors proposed an alternative method for blocking autoantibodies by mutant TNFs (does not bind to TNFR1). The results of this strategy may be to suppress programmed necrosis while reducing the inflammatory load, but maintaining TNF in place, thus preventing tumors and serious infections, such as TB.

All documents mentioned in the present invention are incorporated herein by reference, as if each document were individually recited for reference. It is to be understood that those skilled in the art will be able to make various changes or modifications to the present invention after reading the teachings of the present invention, which also fall within the scope of the claims appended hereto.

REFERENCES

1. Chan, K. F., Siegel, M. R., and Lenardo, J. M. 2000. Signaling by the TNF receptor superfamily and T cell homeostasis. Immunity 13: 419-422.
2. Thoma, B., Grell, M., Pfizenmaier, K., and Scheurich, P. 1990. Identification of a 60-kD tumor necrosis factor (TNF) receptor as the major signal transducing component in TNF responses. J Exp Med 172: 1019-1023.
3. Idriss, H. T., and Naismith, J. H. 2000. TNF alpha and the TNF receptor superfamily: structure-function relationship(s). Microsc Res Tech 50: 184-195.
4. Van Herreweghe, F., Festjens, N., Declercq, W., and Vandenabeele, P. 2010. Tumor necrosis factor-mediated cell death: to break or to burst, that's the question. Cell Mol Life Sci 67: 1567-1579.
5. Kono, H., and Rock, K. L. 2008. How dying cells alert the immune system to danger. Nat Rev Immunol 8: 279-289.
6. Declercq, W., Vanden Berghe, T., and Vandenabeele, P. 2009. RIP kinases at the crossroads of cell death and survival. Cell 138: 229-232.
7. Hitomi, J., Christofferson, D. E., Ng, A., Yao, J., Degterev, A., Xavier, R. J., and Yuan, J. 2008. Identification of a molecular signaling network that regulates a cellular necrotic cell death pathway. Cell 135: 1311-1323.
8. Galluzzi, L., and Kroemer, G. 2008. Necroptosis: a specialized pathway of programmed necrosis. Cell 135: 1161-1163.
9. Vandenabeele, P., Galluzzi, L., Vanden Berghe, T., and Kroemer, G. 2010. Molecular mechanisms of necroptosis: an ordered cellular explosion. Nature Reviews Molecular Cell Biology 11: 700-714.
10. Berghe, T. V., Vanlangenakker, N., Parthoens, E., Deckers, W., Devos, M., Festjens, N., Guerin, C. J., Brunk, U. T., Declercq, W., and Vandenabeele, P. 2010. Necroptosis, necrosis and secondary necrosis converge on similar cellular disintegration features. Cell Death Differ 17: 922-930.
11. Chan, F. K., Shisler, J., Bixby, J. G., Felices, M., Zheng, L., Appel, M., Orenstein, J., Moss, B., and Lenardo, M. J. 2003. A role for tumor necrosis factor receptor-2 and receptor-interacting protein in programmed necrosis and antiviral responses. J Biol Chem 278: 51613-51621.
12. Feldmann, M. 2009. Translating molecular insights in autoimmunity into effective therapy. Annu Rev Immunol 27: 1-27.
13. Scheinfeld, N. 2004. A comprehensive review and evaluation of the side effects of the tumor necrosis factor alpha blockers etanercept, infliximab and adalimumab. J Dermatolog Treat 15: 280-294.
14. Gunther, C., Neumann, H., Neurath, M. F., and Becker, C. 2013. Apoptosis, necrosis and necroptosis: cell death regulation in the intestinal epithelium. Gut 62: 1062-1071.
15. Rock, K. L., and Kono, H. 2008. The inflammatory response to cell death. Annu Rev Pathol 3: 99-126.
16. Linkermann, A., and Green, D. R. 2014. Necroptosis. N Engl J Med 370: 455-465.

The invention claimed is:

1. A light chain variable region ($V_L$) of an antibody, wherein the light chain variable region has Complementarity Determining Region (CDR) comprising:
   $V_L$ CDR1 as shown in SEQ ID NO: 1,
   $V_L$ CDR2 as shown in SEQ ID NO: 3, and
   $V_L$ CDR3 as shown in SEQ ID NO: 5.

2. A light chain of an antibody, wherein the light chain has the light chain variable region according to claim 1 and a light chain constant region.

3. A heavy chain variable region ($V_H$) of an antibody, wherein the heavy chain variable region comprises the following three complementarity determining regions (CDRs):
   $V_H$ CDR1 as shown in SEQ ID NO: 12,
   $V_H$ CDR2 as shown in SEQ ID NO: 14, and
   $V_H$ CDR3 as shown in SEQ ID NO: 16.

4. A heavy chain of an antibody, wherein the heavy chain has the heavy chain variable region according to claim 3 and a heavy chain constant region.

5. An antibody or a recombinant protein comprising at least one polypeptide selected from the group consisting of:
   (1) the light chain variable region ($V_L$) comprising $V_L$ CDR1 as shown in SEQ ID NO: 1, $V_L$ CDR2 as shown in SEQ ID NO: 3, and $V_L$ CDR3 as shown in SEQ ID NO:5,
   (2) the heavy chain variable region ($V_H$) comprising $V_H$ CDR1 as shown in SEQ ID NO: 12, $V_H$ CDR2 as shown in SEQ ID NO: 14, and $V_H$ CDR3 as shown in SEQ ID NO: 16,
   (3) a light chain comprising the light chain variable region and a light chain constant region,
   (4) a heavy chain comprising the heavy chain variable region and a heavy chain constant region, and
   (5) the light chain variable region and the heavy chain variable region,
   wherein the antibody or recombinant protein binds to the sequence QLVVPSE (SEQ ID NO: 27).

6. The antibody or the recombinant protein of claim 5, further comprising
   a tag sequence that assists in expression and/or purification.

7. A polynucleotide encoding the antibody or the recombinant protein of claim 5.

8. A vector, wherein it comprises the polynucleotide according to claim 7.

9. A genetically engineered host cell comprising a vector or a polynucleotide encoding the antibody or the recombinant protein of claim 5.

10. A pharmaceutical composition, wherein it comprises:
    (i) the antibody or the recombinant protein of claim 5, and
    (ii) an optional pharmaceutically acceptable carrier.

11. An inhibitor of the antibody facilitating programmed necrosis of cells,
    wherein the inhibitor is capable of binding to the antibody or the recombinant protein of claim 5.

12. A method for treating an inflammatory disease comprising:
    administering the inhibitor according to claim 11 to a subject in need thereof.

13. A method for diagnosing TNF-cause inflammatory disease of typing a patient with TNF-cause inflammatory disease by the QLVVPSE (SEQ ID NO: 27) fragment, or the antibody or recombinant protein of claim 5, comprising:
    (1) obtaining a sample from a patient;
    (2) detecting whether an anti-TNF autoantibody that specifically binds to the QLVVPSE (SEQ ID NO: 27) fragment or competes with the antibody or the recombinant protein of claim 5 is present in the sample by (a) contacting the sample with the QLVVPSE (SEQ ID NO: 27) fragment and assaying for a specific binding event between the anti-TNF autoantibody and the QLVVPSE (SEQ ID NO: 27) fragment or (b) contacting the sample with a combination of the antibody or recombinant protein of claim 5 and the QLVVPSE (SEQ ID NO: 27) fragment and assaying for a competition between the anti-TNF autoantibody and the antibody or recombinant protein of claim 5 for binding to the QLVVPSE (SEQ ID NO: 27) fragment; and
    (3) when the anti-TNF autoantibody is detected, the patient is typed as having poor prognosis; and when the anti-TNF autoantibody is not detected, the patient is typed as having good prognosis.

14. A test kit for diagnosing an inflammatory disease or typing a patient with TNF-caused inflammatory disease, comprising:
    (a) QLVVPSE (SEQ ID NO: 27) fragment or the antibody or the recombinant protein of claim 5 as a standard; and (b) an instruction on detecting the presence of an anti-TNF autoantibody that specifically binds to QLVVPSE (SEQ ID NO: 27) fragment, or an anti-TNF autoantibody that competes with the antibody or the recombinant protein of claim 5 in a sample from a patient with the QLVVPSE (SEQ ID NO: 27) fragment, or the antibody or the recombinant protein of claim 5 as a standard.

15. The method of claim 13, wherein the TNF-caused inflammatory disease is rheumatoid arthritis, osteoarthritis, or sepsis.

16. The test kit of claim 14, wherein the TNF-caused inflammatory disease is rheumatoid arthritis, osteoarthritis, or sepsis.

17. The method of claim 13, wherein the TNF-caused inflammatory disease is an anti-TNF autoantibody-associated inflammatory disease.

18. The test kit of claim 14, wherein the TNF-caused inflammatory disease is an anti-TNF autoantibody-associated inflammatory disease.

* * * * *